(12) United States Patent
Beaumont et al.

(10) Patent No.: US 9,097,565 B2
(45) Date of Patent: Aug. 4, 2015

(54) METHOD AND APPARATUS FOR MATERIAL FLOW CHARACTERIZATION

(71) Applicant: Beaumont Technolgies, Inc., Erie, PA (US)

(72) Inventors: John P. Beaumont, Harborcreek, PA (US); John Ralston, Painesville, OH (US)

(73) Assignee: Beaumont Technologies, Inc., Erie, PA (US)

( * ) Notice: Subject to any disclaimer, the term of this patent is extended or adjusted under 35 U.S.C. 154(b) by 317 days.

(21) Appl. No.: 13/854,357

(22) Filed: Apr. 1, 2013

(65) Prior Publication Data
US 2013/0255371 A1     Oct. 3, 2013

Related U.S. Application Data

(60) Provisional application No. 61/617,925, filed on Mar. 30, 2012.

(51) Int. Cl.
  *B29C 47/92*   (2006.01)
  *B29C 45/76*   (2006.01)
  (Continued)

(52) U.S. Cl.
  CPC .............. *G01F 1/05* (2013.01); *B29C 45/2703* (2013.01); *B29C 45/76* (2013.01); *B29C 45/77* (2013.01); *G01N 11/08* (2013.01);
  (Continued)

(58) Field of Classification Search
  CPC ........... B29C 2945/76892; B29C 2945/76006; B29C 2945/7604; B29C 2945/76137; B29C 2045/0048; B29C 45/76

USPC .................................. 264/40.1; 425/143–149
See application file for complete search history.

(56) References Cited

U.S. PATENT DOCUMENTS

| 4,118,973 A | 10/1978 | Tucker et al. ...................... 73/55 |
| 4,425,790 A | 1/1984 | Bice et al. ......................... 73/55 |

(Continued)

FOREIGN PATENT DOCUMENTS

| DE | 197 15 630 A1 | 10/1998 |
| DE | 198 48 076 A1 | 4/2000 |

(Continued)

*Primary Examiner* — Lisa Caputo
*Assistant Examiner* — Jonathan Dunlap
(74) *Attorney, Agent, or Firm* — Jonathan M. D'Silva; MacDonald, Illig, Jones & Britton LLP

(57) ABSTRACT

A material characterization system and method for quantifying the characteristics of a flowing thermoplastic material is presented. The system comprises a tool comprising first and second tool halves, a plurality of flowing material characterization channels, and a feed runner. The tool is at a temperature that causes phase changes from fluid to solid in at least a portion of the characterized material and enables solidification of the material in the flowing material characterization channels. The feed runner is connectable to a single flowing material characterization channel. The tool is adjustable to disconnect the feed runner from one flowing material characterization channel and connect it to different flowing material characterization channels. A sensor quantifies the characteristics of the material under different flow conditions. The method comprises measuring the material characteristics as it flows through the flowing material characterization channel at multiple flow rates and repeating measurements for different flowing material characterization channels.

82 Claims, 5 Drawing Sheets

(51) Int. Cl.
  *G01F 1/05* (2006.01)
  *G01N 11/08* (2006.01)
  *B29C 45/27* (2006.01)
  *B29C 45/77* (2006.01)
  *B29C 45/00* (2006.01)
  *B29C 37/00* (2006.01)

(52) U.S. Cl.
  CPC .... *B29C 2037/90* (2013.01); *B29C 2045/0048* (2013.01); *B29C 2945/7604* (2013.01); *B29C 2945/76006* (2013.01); *B29C 2945/7611* (2013.01); *B29C 2945/76056* (2013.01); *B29C 2945/76137* (2013.01); *B29C 2945/76274* (2013.01); *B29C 2945/76287* (2013.01); *B29C 2945/76892* (2013.01)

(56) References Cited

U.S. PATENT DOCUMENTS

| | | | |
|---|---|---|---|
| 4,624,132 A | 11/1986 | Parnaby et al. | 73/55 |
| 5,076,096 A | 12/1991 | Blyler, Jr. et al. | 73/55 |
| 6,023,962 A | 2/2000 | Wang et al. | 73/54.09 |
| 6,464,909 B1 * | 10/2002 | Kazmer et al. | 264/40.1 |
| 6,546,311 B2 | 4/2003 | Brown | 700/200 |
| 6,589,039 B1 * | 7/2003 | Doughty et al. | 425/145 |
| 6,632,079 B1 * | 10/2003 | Kazmer et al. | 425/145 |
| 6,767,486 B2 * | 7/2004 | Doughty et al. | 264/40.1 |
| 6,769,896 B2 * | 8/2004 | Kazmer et al. | 425/145 |
| 7,143,637 B1 | 12/2006 | McBrearty et al. | 73/53.01 |
| 7,632,438 B2 * | 12/2009 | Baumann | 264/40.1 |
| 7,900,503 B2 | 3/2011 | Leonard | 73/54.01 |
| 8,329,075 B2 | 12/2012 | Bader | 264/40.1 |
| 2003/0203064 A1 * | 10/2003 | Doughty et al. | 425/145 |
| 2010/0042339 A1 | 2/2010 | Dodge et al. | 702/50 |
| 2011/0185795 A1 | 8/2011 | Colquhoun | 73/54.02 |
| 2011/0254183 A1 | 10/2011 | Maris-Haug et al. | 264/40.1 |
| 2012/0247190 A1 | 10/2012 | Brown et al. | 73/54.09 |
| 2012/0294963 A1 | 11/2012 | Altonen et al. | 425/149 |
| 2012/0329948 A1 | 12/2012 | Altonen et al. | 525/56 |

FOREIGN PATENT DOCUMENTS

| | | |
|---|---|---|
| DE | 102 15 946 A1 | 11/2003 |
| JP | 64-87316 | 3/1989 |
| JP | 2003-262579 | 9/2003 |
| JP | 2011-240631 | 12/2011 |
| WO | WO 2012/038769 A1 | 3/2013 |

\* cited by examiner

METHOD AND APPARATUS FOR MATERIAL FLOW CHARACTERIZATION

This application takes priority from U.S. provisional application No. 61/617,925 filed Mar. 30, 2012, which is incorporated herein by reference.

BACKGROUND

When selecting a thermoplastic material for the development and manufacture of injection mold plastic parts, one must consider both the application requirements and the manufacturability of the selected material. One critical consideration when selecting a material for manufacturability is determining the "injection moldability"—how that material will flow or mold within the plasticating injection unit. To determine injection moldability, measurements that quantify the characteristics of that material are essential. Such characteristics include pressure per inch of flow, development of a frozen layer, flow rate, viscosity, shear rate, which all help to paint an accurate picture of how a material will actually flow or mold within the plasticating injection unit.

There are three methods that are commonly used measuring injection moldability. The most common is the Melt Flow Index (MFI) test due to its low cost, but it provides the most limited and irrelevant results in regards to its application for understanding how a melt will flow in an injection mold. A second method is a capillary rheometer, which is designed to capture the non-Newtonian viscosity characteristics of a thermoplastic material under a wide range of shear rates that the MFI test lacks. Both of these methods are highly limited because they are isothermal extrusion tests which will not capture the significant influence of a relatively cold mold acting to cool a flowing material as it is flowing through the mold's channels.

To the molder and the processor, the detailed viscosity vs. shear rate data provided by a capillary rheometer is fairly abstract and does not provide much value. The data is provided as viscosity vs. shear rate, possibly at multiple melt temperatures. Common viscosity units include psi-sec and pascal-sec. Shear rate is expressed as reciprocal seconds ($sec^{-1}$ or $1/sec$). In either case, the viscosity and shear rate is expressed in somewhat abstract units that are not helpful to the product developer or molder. They are interested in how much pressure it will take to fill a mold having varied runner and part forming cavity geometries used to produce a given part. Therefore even if the test method was non-isothermal, the expressions of viscosity and shear rate do not provide meaningful information. As a result this data by itself is rarely used by those in product development or manufacturing.

The third common method used to evaluate how a plastic material will flow through an injection mold is the use of injection molding simulation programs. Injection molding simulation programs utilize the classic viscosity vs. shear vs. temperature data derived from a capillary rheometer and combines this with other material characterization tests to attempt to mathematically model the materials flow characteristics flowing through a relatively cold mold. There are numerous challenges to this mathematical modeling of which a significant part is the material characterization methods on which the programs are dependant. These characteristics can include thermal conductively, melt and solid phase densities, pressure-specific volume-temperature characteristics (P-V-T), specific heat, etc. Many of these are variables that cannot be accurately measured under the conditions that exist in injection molding. An example would be P-V-T data which is captured while temperature changes are commonly only 3° C. per minute. This is in contrast to actual performance where a thermoplastic material forms a frozen skin when the plastic experiences temperature drops from a molten temperature which is commonly about 250° C. in the plasticating injection unit to what is commonly less than 50° C. in a flow channel in the mold in small fractions of a second. These actual cooling rates are therefore in the range of a few hundred degrees per second to more than a thousand degrees per second. As a result of the complex characteristics of plastic materials as they flow through the mold and the difficulty in modeling these characteristic for use in an injection molding mold filling simulation program, there is an inherent error in the ability of molding simulation programs to accurately predict mold filling pressures. Predicting mold filling pressures are very important to the users of injection molding simulation programs and the plastics injection molding industry as a whole.

Other methods have been developed to evaluate the viscosity characteristics of a plastic material as influenced by non-isothermal conditions. One such device disclosed in PCT Publication Number WO 2012/038769 does this by using a mold with a measuring capillary channel in the moving half of the mold and sensors in the stationary half of the mold. The capillary channel opens at one end to allow the material flowing through the measurement channel to flow through the capillary to atmosphere. The injection rate is controlled and determined by an injection molding machine that injects the material through the capillary section of the mold. Melt temperatures and pressures are measured with sensors. Shear rates can be calculated by assuming the flow rate from the injection molding machine to be the same as that flowing through the capillary and knowing the channel cross section. Shear stress can be calculated by knowing pressures and channel cross sectional shape. Calculated shear rate and shear stress can then be used to calculate viscosity. The mold can be cooled to run isothermal rheological tests and the mold opened to remove the sample material after it has solidified. The capillary channels are in mold inserts that can be removed by opening the mold, unscrewing attachment bolts, and replacing the capillary channel insert with an alternate insert with another capillary geometry enabling the study of various viscosity characteristics and applying various corrections factors commonly required and applied to the rheological characterization of a plastic material. Though this method is an improvement over many other rheological flow characterization methods, it does not address a number of fundamental needs of the injection molding industry addressed by the qualities of the methods of the invention disclosed herein.

U.S. Pat. No. 5,076,096 to Blyler, Jr. et al. (hereinafter "Blyler") discloses a process and apparatus for measuring viscosity of a thermosetting composition, which has some of the same limited utility as discussed above. The Blyler apparatus is also limited in its applicability to materials that are thermosetting compositions. Thermosetting materials require a relatively cool polymer to be injected into a relatively hot mold, the hot mold accelerating a chemical reaction where the thermosetting material will cross link. This is very different than the conditions required for thermoplastic materials. Thus using any other kind of material would be beyond the limitations of what is claimed and taught.

Blyler also discloses two different modes of measuring the viscosity of a thermosetting: an isothermal mode and a non-isothermal mode. In the isothermal mode, the preheated thermosetting resin is placed in a heated reservoir where it becomes a fluid and is forced through the mold and capillary. The thermosetting resin, reservoir, and mold are all heated to the same temperature (See Blyler col. 4, lines 15-22). In the non-isothermal mode, the thermosetting resin is preheated to a temperature lower than the temperature of the mold (See Blyler col. 5, lines 42-45). In this non-isothermal mode, the thermosetting material flows through a hot mold runner and capillary. Therefore, neither mode discloses that the thermosetting is heated at a temperature higher than the temperature of the mold through which it will flow. Measuring thermosetting material flows at low isothermal temperature conditions causes inaccuracies in the measurements because the thermosetting material will not be able to initiate the normal chemical reaction to begin cure in the flowing material nor form a solidifying skin as it flows through the capillary, which is much more likely to occur under non-isothermal flow conditions using a relatively hot mold.

Other prior art methods and apparatuses make measurements of material flow conditions prior to the material entering a flow channel through which the material ultimately flows. Taking measurements prior to the material entering a flow channel creates greater error in the calculations of the characteristics of the material. The measurements taken are only a prediction of how the material will flow through the flow channel and mathematics and/or a multitude of additional tests must be used to make adjustments for any real world factors that cannot be calculated based on those predictions. Using mathematical calculation corrections, sometimes known as fudge factors, will always have some level of inaccuracy because there are always variables that cannot be factored by mathematical equations. Common mathematical calculation corrections used in these circumstances are the Bagley Correction or the Rabinowitsch Correction.

U.S. Pat. No. 6,023,962 to Wang et al. (hereinafter "Wang") for example discloses a process and apparatus for testing the rheological properties of resins. Wang discloses that the apparatus comprises a mold having a mold cavity that resin first enters into, a slit, a thermocouple device positioned within the cavity near the slit, and a pressure transducer within the reservoir or reservoir walls (see Wang col. 4, lines 48-67). To measure the rheological properties of the resin, the pre-heated liquid resin enters into and is heated within the mold cavity to a high temperature and, once heated, is then extruded through the slit, while the pressure transducer or thermocouple device measures the pressure within the reservoir (See Wang col. 8, lines 45-60). Therefore, the measurements of the resin are also taken prior to the resin's entering of the slit and not while the resin is flowing through the slit.

It should be noted that in the embodiment of the apparatus that discloses multiple reservoirs on a single mold plate, each reservoir is filled with resin simultaneously and in turn the resin flows through the slit connected to each reservoir so that one can obtain viscosity data at different shear rates simultaneously, as opposed to flowing the resin each through slit in sequence (see Wang col. 6, lines 49-57). This configuration requires a multitude of sensors for each reservoir. Each of the multitude of reservoirs require individual loading of material into each reservoir. Also the different pressures required to drive the fluid thermosetting material simultaneously through the multiple strips could create numerous mechanical problems due to uneven distributions of pressure and force requirements of what may be assumed to be a primary injection ram driving all of the multitude of pistons for each of the reservoirs.

Other prior art methods and devices are used for monitoring, documentation, or control of specific injection molding machines that are in operation to manufacture an injection molded plastic product. These methods and devices are not used for a general understanding or characterization of the material, but to check on the performance of a plasticating injection unit producing a commercial product. U.S. Pat. No. 8,329,075 to Bader (hereinafter "Bader") for example discloses a method for determining the viscosity of a material in an injection mold of an injection molding machine. The method is particular to viscosity determinations within a specific injection molding machine being used to manufacture a specific product in a commercial mold. The shear rate and shear stress values calculated for viscosity calculations are actually not true values of shear rate, shear stress, or viscosity as the channel cross sections of the cavity producing the commercial part will continually vary. Therefore the values calculated are the culmination of a wide range of actual viscosity conditions that will occur in the melt as it flows through these varied geometries. This is very different from methods whose purpose is to characterize the flow characteristics of a polymer. The subject matter does not apply to directly quantifying the characteristics of materials themselves, but rather is intended to "monitor, and possibly control, an injection molding process under practical conditions" (see Bader col. 2, lines 38-40).

The use of classic fundamental rheological characterization models of a plastic materials has limited use to those in the injection molding industry. Classical rheological characterization data does not provide an accurate means to determine how a plastic material will fill a mold without the use of complex and expensive mold filling simulation programs. The economics of an accurate material characterization test is an important consideration for the industry. With well over 100,000 variations of commercial thermoplastic materials, the cost to characterize a material must be kept to a minimum without compromising the quality and usability of the data. These variations in polymer materials are not limited to polymer type. A plastics material's mold filling characteristics are dependent on numerous variables including material type, blends of materials, copolymers, molecular weight, molecular weight distribution, additive types, and percentage of additives. Under non-isothermal conditions of the injection molding process a rheological value is not relevant. The resistance to flow through a runner or cavity channel will vary not only with the flow rate and temperature of the material, but also with the cross sectional size and thickness of the channels. This is in contrast to isothermal tests where the rheological characteristics are constant regardless of cross sectional dimensions. It is typical that the rheological characterization of a given material be conducted on ether a MFI with a single diameter capillary or on a capillary rheometer with a single diameter capillary. This is not characteristic of what would happen in non-isothermal conditions where the cross section will influence the heat exchange between the molten material and channel boundaries. There is also a need in the industry to provide an economical means to verify the accuracy of mold filling simulation programs in simulating the flow and pressure conditions through the geometry of a mold being analyzed.

By relying on calculations based on the injection rate of an injection unit, prior art methods described above do not accurately capture the material flow rates, velocities, and shear rates through a flow measurement channel. There are a number of sources of error in these methods. One is the fact that melted plastic material is compressible under the high pressure experienced during actual injection molding. This compression can be over 20%. As a result the flow rate as determined by the velocity of the injection piston or screw used to inject molten material through a flow measurement channel will not be the same as the actual flow rate through the flow measurement channel. Additionally there can be leakage of molten material past the injecting piston or screw. In plasticating injection units that utilize an injection molding screw, there can be a number of additional issues which will cause the indicated injection rate determined by screw advancement velocity to be a poor indicator of actual injection rate through a downstream flow channel. One is that in practice, after a charge of material has been developed for injection, the screw is pulled back (generally referred to as suck back) so that the material does not drool out of the machines nozzle. This fully decompresses the molten material and, depending on the amount of suck back, will vary the actual amount of material being injected into a mold once the screw moves forward to drive the molten material into the mold. Additionally plasticating injection units typically use some form of check ring or check valve to prevent back flow over the screw flights during injection when the screw is driven forward. During plastification and from suck back, these valves are in a forward open position. As the screw advances forward to inject the molten material, the valves will move backward in order to seat and thereby help prevent molten material from leaking back into the screw flights. This shift will influence actual flow rate. Finally, there is expected to be some leakage over these check rings during injection molding. All combined, there can be significant variation between flow rate expected based on the screws injection velocity and the actual flow rate through the mold or a melt measurement channel.

Unlike the prior art methods and apparatus discussed above, what is presented is a new method and apparatus for quantifying the characteristics of a flowing thermoplastic material melted into a fluid state by a plasticating injection unit. The melted thermoplastic material is injected at different flow rates through flowing material characterization channels having cross-sections of different geometries. The characteristics of the material are measured within these flowing material characterization channels. This method and apparatus determines the characteristics of the material itself, not just the characteristics of the material in a specific injection molding machine.

SUMMARY

What is presented is a method and apparatus for quantifying the characteristics of a flowing thermoplastic material melted into a fluid state by a plasticating injection unit. The system comprises a tool comprising a first tool half, a second tool half, a plurality of flowing material characterization channels, and a feed runner having a flow path to the plasticating injection unit. The tool is at a temperature that causes phase changes from fluid to solid to occur in at least a portion of the material being characterized and that enables solidification of the material in the flowing material characterization channel. Each flowing material characterization channel has a first end, a second end, and a predefined channel cross-section. The feed runner is connectable to a single flowing material characterization channel in succession at the first end, creating a material flow path from the plasticating injection unit to the flowing material characterization channel. The tool is adjustable to disconnect the feed runner from the flowing material characterization channel and connect the feed runner to a different flowing material characterization channel. A sensor in the system quantifies the characteristics of the material under different flow conditions.

In various embodiments, the plurality of flowing material characterization channels are impressed into an adjustable and movable cartridge. Adjustment of the tool is done by adjusting the cartridge. Such a cartridge would be adjustable, either manually or with an actuator, to connect a different flowing material characterization channel to the feed runner to enable characterization of the material within different predefined channel cross-section geometries.

Various methods of quantifying the characteristics of a flowing thermoplastic material to determine its behavior in a plasticating injection unit are also presented. In general a flowing material characterization channel having a predetermined cross-sectional geometry is connected to a plasticating injection unit. The material to be characterized is melted into a fluid state with the plasticating injection unit. The material is flowed through the flowing material characterization channel at multiple set flow rates and the material characteristics are measured through the flowing material characterization channel at each of the multiple set flow rates. The process is repeated for different flowing material characterization channels, each having an individual predetermined cross-sectional geometry. Additional information such as the velocity of the material flowing through each flowing material characterization channel, the volumetric flow rate of the material, the pressure per inch of flow of the material, the characteristics of a developing frozen layer of material skin can also be measured or calculated. From these measurements a material characterization profile is developed.

The measurements taken in such a way can be used for many purposes. They could be incorporated into a mold filling simulation program or used to validate the predicted material behavior of other mold filling simulation programs. The measured material characteristics could be presented in graphical format, in tabular format, or any other useful way. The methods provide a way of evaluating the performance of plasticating injection units through the quantified characteristics of the material from each flowing material characterization channel.

Those skilled in the art will realize that this invention is capable of embodiments that are different from those shown and that details of the devices and methods can be changed in various manners without departing from the scope of this invention. Accordingly, the drawings and descriptions are to be regarded as including such equivalent embodiments as do not depart from the spirit and scope of this invention.

BRIEF DESCRIPTION OF DRAWINGS

For a more complete understanding and appreciation of this invention, and its many advantages, reference will be made to the following detailed description taken in conjunction with the accompanying drawings.

DETAILED DESCRIPTION

Figure 1A:
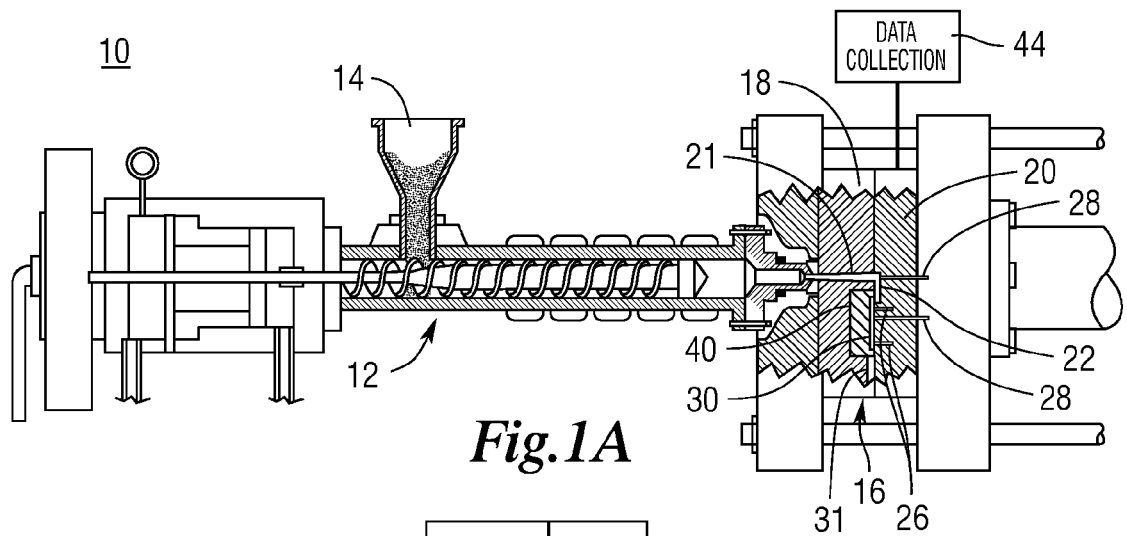
FIG. 1A is a side view of the material characterization system comprising a plasticating injection unit that is an injection molding machine.

Referring to the drawings, some of the reference numerals are used to designate the same or corresponding parts through several of the embodiments and figures shown and described. Corresponding parts are denoted in different embodiments with the addition of lowercase letters. Variations of corresponding parts in form or function that are depicted in the figures are described. It will be understood that variations in the embodiments can generally be interchanged without deviating from the invention.

As shown in FIG. 1A, a material characterization system 10 is used to quantify the characteristics of a material. The material is first introduced to a plasticating injection unit 12, in this case, an injection molding machine (although any system that is capable of melting a plastic material and injecting it into a tool as described herein would suffice), through a hopper 14 located on the plasticating injection unit 12. The plasticating injection unit 12 then heats the material until it melts into a fluid state. Typically the material to be characterized is some variety of thermoplastic, but it should be understood that other materials such as thermosets, elastomers, and/or other polymers, etc. may be characterized. The plasticating injection unit 12 pushes the material toward a tool 16 that is connected with the plasticating injection unit 12. The characteristics of the material are quantified while within the tool 16.

The tool 16 generally comprises two tool halves that can be opened, a first tool half 18 and a second tool half 20. As best understood by comparing FIGS. 1B, 2, and 3A, the first tool half 18 has a sprue 21 feed runner 22 that is typically centrally positioned on the first tool half 18. The sprue 21 is a burrowed opening that runs entirely through the first tool half 18 from the plasticating injection unit 12. The sprue 21 connects to a feed runner 22 that is located on the second tool half 20. The sprue 21 can either be a cold sprue or a hot sprue. Material injected into a cold sprue will solidify with the material in the feed runner 22 portion and in the flowing material characterization channels 30 after each individual material characterization test. Material injected through a hot sprue will remain molten in the hot sprue at all times. The cold sprue 21 has a slight outward taper from the plasticating injection unit 12 to the feed runner 22. The feed runner 22 functions as a conduit connecting the plasticating injection unit 12 to one of the flowing material characterization channels 30.

Figure 3A:
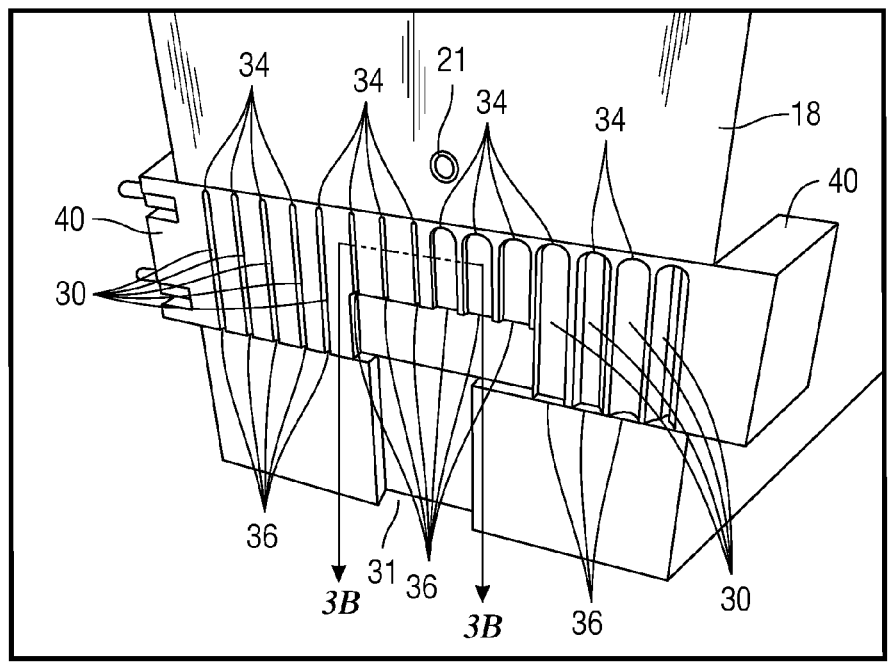
FIG. 3A is a perspective view of an embodiment of a first tool half.
Figure 3B:
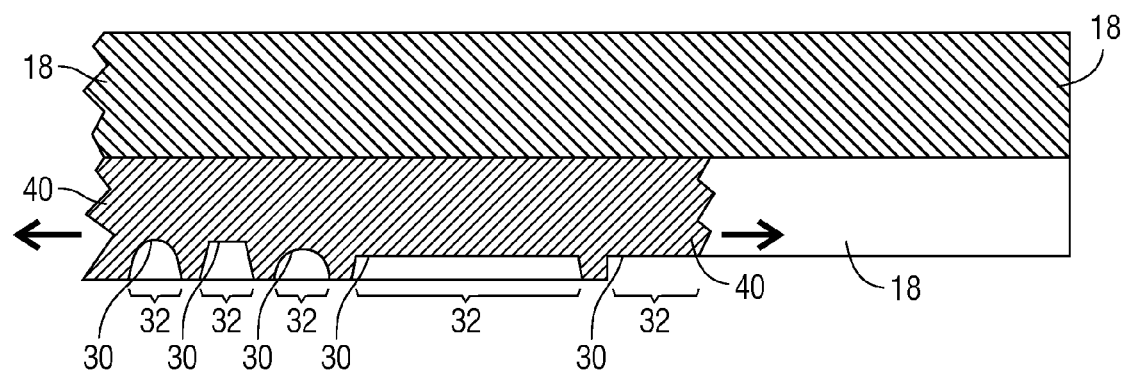
FIG. 3B is a cross section of the cartridge of the first tool half of FIG. 3A.

As shown in FIGS. 3A and 3B, the first tool half 18 has an adjustable and removable cartridge 40 that comprises a plurality of flowing material characterization channels 30 impressed into it. One having ordinary skill in the art will see that the plurality of flowing material characterization channels 30 can be directly impressed into the first tool half 18 without the cartridge 40 with that the tool 16 in its entirety being the adjustable element. Although impractical to do, it will be understood that the tool 16 could be oriented in such a manner that the second tool half 20 comprises the cartridge 40 with the plurality of flowing material characterization channels 30 and the first tool half 18 comprises a sensor 24 and an additional sensor 26, while still achieving similar results from the system.

Figure 2:
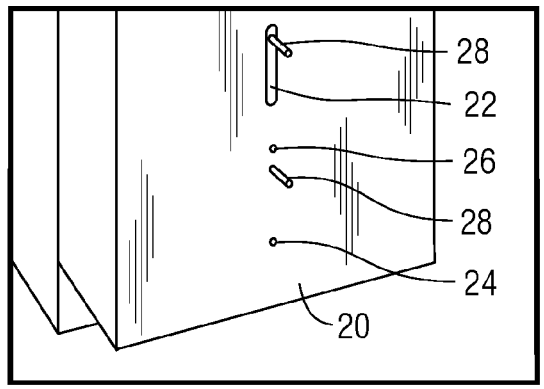
FIG. 2 is a perspective view of a second tool half.

As best understood by comparing FIGS. 1A, 2, and 3A, when both the first tool half 18 and second tool half 20 are inserted into the material characterization system 10, the plurality of flowing material characterization channels 30 are all encapsulated along a central plane within the tool 16. However the feed runner 22 only provides a fluid connection from the plasticating injection unit 12 to a single flowing material characterization channel 30. A purge slot 31 is incorporated into the first tool half 18 which allows for those embodiments of flowing material characterization channels 30 that are open to the atmosphere to purge fluid material out of the tool 16 (discussed in more detail below). Each flowing material characterization channel 30 comprises a first end 34 and a second end 36.

As best shown in FIG. 3B, each flowing material characterization channel 30 has its own predefined channel cross-section 32 geometry. The two most common geometries in an injection mold can be characterized as runner-like and those that are cavity-like. Runner-like geometries are most commonly full round, trapezoidal or modified parabolic geometries. Cavity-like geometries are normally relatively shallow wide channels. Runner like-channels can range in size from very small 1 mm diameter (or smaller) used with very easy flowing polymers like LCP's and in micromolding applications, to much larger channels that can be over 6 mm diameter. Similarly part forming cavity wall thicknesses can be very thin, having thicknesses less than 0.5 mm to over 6 mm. When the tool 16 is installed within the material characterization system 10, the side of each predefined channel cross-section 32 against the second tool half 20 is entirely flat; whereas, the side of each predefined channel cross-section 32 impressed into the first tool half 18 forms the shape of each predefined channel cross-section 32 geometry. The geometry of the predefined channel cross-sections 32 of the flowing material characterization channels 30, as shown in FIG. 3B, are circular, rectangular, trapezoidal, and parabolic (as discussed above); each geometry is uniform from the first end 34 to the second end 36 of its respective flowing material characterization channel 30. It will be understood that other geometries of the predefined channel cross-sections 32 may be used within the material characterization system 10.

The cartridge 40 can be adjusted by an actuator device (not shown) that allows for the user to adjust the cartridge 40 without having to remove the entire tool 16 from the system. The actuator may make adjustments of the cartridge 40 manually or automatically. When the cartridge 40 is adjusted, the feed runner 22 can be directed to create a material flow path with a different flowing material characterization channel 30. The cartridge 40 can be swapped out entirely with another one that has a different set of flowing material characterization channels 30, each with different predefined channel cross-section 32 geometries. This allows for quicker and less expensive characterization of a material with the method described herein.

The second end 36 of each of the plurality of flowing material characterization channels 30 varies in each flowing material characterization channel 30. A number of the flowing material characterization channels 30 have a second end 36 that is closed off, allowing for those flowing material characterization channels 30 to be completely sealed and pressurized. Other flowing material characterization channels 30 have a second end 36 that opens to the surrounding atmosphere and purge material into the purge slot 31 which allows for characterization for materials under those conditions. Having the ability to quantify the characteristics of the material in a pressurized flowing material characterization channel 30 and in a non-pressurized flowing material characterization channel 30 can give a broader understanding of the flow characteristics of the material.

The system and method described herein provides an efficient and economical means to map the mold filling characteristics of polymer material under a wide range of processes and through a variety of geometries. The method includes a means to plasticate and inject a laminar flowing material, having properties which will experience a fluid to solid phase change during and after molding, sequentially through a variety of relatively cold flow geometries that are representative of temperature and channel geometries found in an injection mold. Thermoplastic and thermosetting plastic materials are highly complex and exhibit pseudoplastic non-Newtonian shear thinning, temperature sensitive viscosities, and rate sensitive phase changes (from fluid to solid). The phase change in a thermoplastic flowing material begins at the boundary of the hot melt and the relatively cold channel boundaries. In these conditions a "frozen" solid skin will develop. This phase change with semi-crystalline thermoplastic materials can be particularly complex due to the latent heat of fusion resulting from the crystal formation of the solidifying semi-crystalline polymer. While the material characterization system 10 is in operation, the temperature of the tool 16 is at a temperature that causes phase changes from fluid to solid to occur in at least a portion of the material being characterized and that enables solidification of the material in the flowing material characterization channel 30. Setting the tool 16 to a sufficiently lower temperature than that used to melt the material creates a non-isothermal condition in the flow path 22 of the material from the plasticating injection unit 12 to the second end 36 of the flowing material characterization channel 30. The tool 16 may be heated so that both the first tool half 18 and said second tool half 20 are each at a temperature that enables complete solidification of the material in the flowing material characterization channel 30 by the point at which the material reaches the second end 36. Although the tool 16 can solidify most thermoplastic materials at room temperature, or one lower than room temperature, it will be understood that the solidification temperature could be well over room temperature. The tool 16 could solidify certain materials at temperatures upward of 400 degrees Fahrenheit. An example of solidifying materials at 400 degrees Fahrenheit would be for a thermoplastic material that is melted and processed at a temperature somewhere between 700-800 degrees Fahrenheit. Additionally, thermosetting plastic materials generally require a temperature that is relatively higher than the melting point of the material in order for these types of materials to solidify.

Figure 1B:
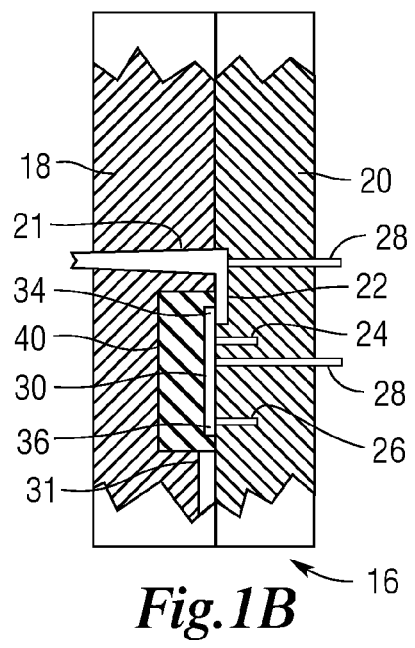
FIG. 1B is a close up view of the tool of the a plasticating injection unit of FIG. 1A.

FIGS. 1B and 2 shows a number of ejection pins 28 positioned in the second tool half 20. The ejection pins 28 are normally retracted, so as to not interfere with the material flowing through the flow channels in the mold 16, as shown in FIG. 1B while the mold is closed and material is flowing through the flow channels. There can be a different number of ejection pins 28 than shown. After the material being characterized has solidified in the sprue 21 (if it is a cold sprue as described above), the flow runner 22, and the flowing material characterization channel 30, the mold 16 is opened to allow removal of the solidified material. The ejector pins 28 push out (as shown in FIG. 2) and assist with the ejection. The mold 16 is then reclosed and the system is ready to run the next test. Those of skill in the art will understand that the number, location, and arrangement of ejector pins 28 can be varied depending on the specific application. As best seen in FIG. 1B, one of the ejector pins 28 is located in the feed runner 22 directly opposite the sprue 21. In embodiments in which the sprue 21 is not heated, an undercut (not shown) could be incorporated into the feed runner 22 or into the housing in which ejector pin 28 is located so that the material fills the undercut during the flow characterization test. The solidified material in the undercut anchors the material in the second tool half 20 so that when the mold 16 is opened after the flow characterization test, the undercut helps extract the solidified material out of the sprue 21 from the first tool half 18 before the ejector pin 28 ejects the material from the mold 16. This undercut can be applied at any of the ejector pins 28, if it is found that additional assistance will be needed for ejection of the solidified material. It will be appreciated by those of skill in the art that in embodiments in which the cartridge 40 is included in the second tool half 20, ejector pins 28 will have to be incorporated into each of the plurality of flowing material characterization channels 30.

In the embodiment shown in FIGS. 1A through 2, a variety of sensors are used for measuring material characteristics under different flow conditions as the material is forced under pressure from the plasticating injection unit 12 flows through the flowing material characterization channel 30. These sensors are typically incorporated somewhere in the tool 16 and connected to a data collection system 44 that records, stores, and/or processes sensed data. In the embodiment described here, a sensor 24 and additional sensor 26 are incorporated within the second tool half 20. Each of the sensors is typically positioned within the body of the second tool half 18. The sensor 24 and additional sensor 26 could also be positioned elsewhere, such as within the first tool half 18, so long as they are able to make accurate measurements of material conditions. It will also be understood that the sensor 24 and additional sensor 26 could be at any type of sensor, such as a transducer, pressure sensor, pressure trace, temperature sensors, position sensor, etc. It will be understood that the actual number and composition of sensors could be varied within the system so long as there is at least one sensor that is capable of quantifying the characteristics of the material under different flow conditions.

The information provided by the sensors can be used to determine the travel time of the material as it flows between the sensor 24 and additional sensor 26 within the flowing material characterization channel 30. The velocity of the flowing material is measured through the sensor 24 and additional sensor 26 measuring the position of the material within the flowing material characterization channel 30. Because the material in its fluid state is hotter than the surrounding tool 16, a temperature spike is easily registered as the material flows past the sensor 24 and additional sensor 26. The sensor 24 will register a temperature spike in the flowing material characterization channel 30 at the first location and when the material flow reaches the additional sensor 26 it will measure the temperature spike at its second location. The time of activation of the temperature change at the sensor 24 and additional sensor 26 is also recorded. Incorporating this information into the following equation provides the flow velocity of the material:

$$V = \frac{\Delta x}{\Delta T}$$

where V is velocity, $\Delta x$ is the displacement of the flow of material, which in this system is the distance between the sensor 26 and the additional sensor 26, and $\Delta T$ time interval between temperature spike readings from the sensor 26 and the additional sensor 26.

The volumetric flow rate of the material within the flowing material characterization channel 30 can then be calculated by the following equation:

$$Q = V \times \delta$$

where Q is the volumetric flow rate of the material within the flowing material characterization channel 30, $\delta$ is cross sectional area of the flowing material characterization channel 30 in inches², and V is velocity of the material within the flowing material characterization channel 30 in inches/second.

Next, the shear rate is calculated by the following equation:

$$\gamma = \frac{4Q}{\pi r^3}$$

where $\gamma$ is the shear rate, and r is the radius of a circular flowing material characterization channel 30.

Next, the shear stress is calculated by the following equation:

$$\sigma = \frac{\Delta P r}{2L}$$

where $\sigma$ is the shear stress, $\Delta P$ is the pressure change between the sensor 24 and additional sensor 26, and L is the distance between the sensor 24 and additional sensor 26. Those having ordinary skill in the art will understand that different equations for shear stress and shear rate calculations are needed for flowing material characterization channels 30 that have different predefined channel cross-section 32 geometries.

Finally, the viscosity is calculated by the following equation:

$$\eta = \frac{\sigma}{\gamma}$$

where $\eta$ is the viscosity. It will be understood that Bagley corrections may not be required for the above calculations dependent on positioning of sensors within the flowing material characterization channel 30, as they are required in prior art calculations, for example in traditional capillary rheometers. Each of the above calculations is essential for quantifying the rheological characteristics of a material within the material characterization system 10.

If the system implements pressure sensors, pressure per inch of flow (psi/inch) can be determined for a variety of predefined channel cross-sections 32. As example is a rectangular cross section similar to the predefined channel cross-section 32 of the flowing material characterization channel 30 shown in FIGS. 3A and 3B which has a predetermined thickness, width, and length. Pressures and fill velocities can be measured along one or more sections of the length of the flowing material characterization channel 30. If pressure along a 4-inch length is measured to be 4,000 psi, then the pressure per inch of flow is approximately 1,000 psi/inch. Pressure development and distribution along this 4-inch length will be significantly linear (i.e., each inch of length will experience approximately 1,000 psi of pressure). If this is not linear, an indication could be provided by having additional sensors along the length of the flowing material characterization channel 30. Velocity along this length will also be significantly linear as long as the material pressures have not exceeded the injection pressure limits of the plasticating injection unit 12 and that the plasticating injection unit 12 delivers the material at a constant injection rate. Knowing the pressure per inch of flow of a particular material for a given channel cross-section, material and tool temperature, and injection velocity, this information can be used to calculate the pressure loss that the same material will experience across an unrelated mold cavity having similar wall thickness, flow velocity, and temperatures.

The measure of psi/inch will have the highest accuracy with channel lengths within, or close to, the length of the flowing material characterization channel 30. Channel widths are a secondary consideration as long as the material flow velocity is the defining term for flow. For example, in two parts of the same flow length the first is gated from one end of a 5-inch strip that is 1-inch wide and the second has a center gated disk having a 5-inch radius. In both cases the flow length from the gate to the end of the fill is 5-inches. If fill is defined with a fill velocity of 5-inches per second, then both parts will fill in one second, even though each part will experience very different volumetric flow rates.

Extrapolating the psi/inch measurements to lengths beyond the measured flow lengths will be most accurate at "critical velocities"—where the thermal balance between heat gains in the material versus heat lost to the colder flow boundaries is significantly balanced. Under critical velocity conditions the material temperature is relatively constant as it flows through the flow channel and the development of a plastic frozen layer along the flow channel boundaries becomes stabilized as discussed below.

During the injection molding process, a thermoplastic material is melted in the plasticating injection unit 12 and injected into the relatively cold tool 16. The temperature of the tool 16 is set to a temperature that will allow the material to transition from a molten condition to a solid plastic part (as discussed earlier, this temperature could be well above room temperature). The flow of thermoplastic material during the injection molding process is laminar. As the laminar flowing material flows through the cold tool 16, it experiences heat loss to the relatively cold walls of the feed runner 22 and the flowing material characterization channel 30. The melted material nearest the cold wall will freeze creating a solid layer of "frozen" material that changes the cross sectional size of the flowing material characterization channel 30. The material will now be flowing between the frozen layers of material in the flowing material characterization channel 30. In contrast is the development of frictional heat developed by the relative movement of the flowing material to the stationary mold walls. This frictional heating can increase material temperature between flowing laminates of the laminar flowing material.

Time, the temperature of the tool 16, the temperature of the material, the shape of the flow channel, and the shear conditions between the laminar flowing material and the stationary relatively cold flow channel wall will influence the development of the frozen layer in the outer laminates between the laminar flowing material and the relatively lower temperature flowing material characterization channel 30. In turn the thickness and conditions of this developing frozen layer will influence the flow characteristics of the plastic material as well as the flow channel conditions themselves. For example, a slow flowing material will have low shear conditions and longer exposure to the relatively cold walls. This will increase the development of a frozen layer more than a fast flowing material. The resultant thicker frozen layer will further reduce the cross sectional size of the flow channel, changing its geometry and thereby significantly influence the pressure to the flow through the decreasing flow channel cross section. The thickening frozen layer however also increases the distance between the flowing material and the cold wall and will slow the rate of heat transfer to the flowing material. At the same time the decreasing flow channel cross section and its changing geometry can cause an increase in the shear rate when the plasticating injection unit 12 is delivering material to the flowing material characterization channel 30 at a constant controlled injection rate. The result is a very complex balance of thermal conditions, influencing the flow characteristics of a laminar flowing plastic material, within the flowing material characterization channel 30. These complex interactions make it very difficult to predict how plastic will flow through a tool 16. This is evidenced by the fact that mold filling simulation programs have been in commercial application and development for nearly 40 years and still can have significant error in even relatively simple geometries. Note that this problem exists despite the ability to model the non-Newtonian viscosity characteristics of the material using state-of-the-art prior art isothermal rheometers.

Prior art isothermal rheometers provide a means of characterizing a thermoplastics flow characteristics without the formation of a frozen layer. Data derived using prior art traditional state-of-the-art rheometers can be used in conjunction with the material characterization system 10 described herein to facilitate components of characterizing the development of a frozen layer that occurs in flowing melted material during normal injection molding processes. This, in part, can be performed by contrasting the flow characteristics developed using the two methods.

At a given shear rate and material temperature the flow data from a traditional prior art isothermal rheometer will be relatively constant regardless of the cross sectional shape of the flow measurement channel. This is in contrast to the material characterization system 10 described herein where the geometry of the predefined channel cross-section 32 of the flowing material characterization channel 30 will cause a calculated viscosity to vary at the same shear rate and material temperature due to the difference in thermal exchange between the flowing material and the relatively cold flowing material characterization channel 30. Contrasting the relatively constant rheological data from a traditional prior art rheometer at a given shear rate and temperature and the data generated by the material characterization system 10 described herein under the same melted material conditions will help isolate the influence of the developing frozen layer of the material.

Further, using the material characterization system 10 described herein it has been found that pressure along a given length (pressure per length of flow) will change dependent on the continuing downstream flow conditions after a given flowing material characterization channel 30 length and the duration of flushing flow through a flowing material characterization channel 30 section. Flowing material characterization channels 30 could show material performance under different flow characterization conditions, such as a continuing length of channel of the same cross section, a changing cross sectional length, and/or an open ended channel where the material can purge to atmosphere or some negligible pressure developing flow path or chamber. This change in pressure within a section of the flowing material characterization channel 30 resulting from the influence of continuing downstream flow conditions provides information regarding factors influencing the flow resistance provided by a developing frozen layer of a given laminar flowing material and its influence on the flow of a material through a non-isothermal channel.

With the material characterization system 10 disclosed herein, it will be possible to measure the characteristics of both the developing frozen layer as well as that of the laminar flowing material flowing through the frozen layer boundaries, developed around the perimeter of the flowing material characterization channel 30, at multiple volumetric flow rates. In order to better characterize the material, measurements and calculations of pressure per unit length of flow, shear stress, and viscosity can be taken to further develop the material characterization profile.

It will be understood that as few as one sensor, preferably a pressure sensor, could be used to quantify the characteristics of the material. When one sensor is used, the calculations can be made by relying on the volumetric flow rate determined from the plasticating injection unit 12 to calculate velocity, volumetric flow rate, and/or shear rate of the material. Using pressure sensors in the flowing material characterization channel 30 allows for measuring the material pressure development as the material flows through flowing material characterization channels 30 that are not open to atmosphere, as discussed below.

A thermoplastic material is characterized using the material characterization system 10 described herein requires the plasticating injection unit 12 to first melt the material into a fluid state and then flowing the material into material characterization tool 16. Material flows through the sprue 21 in the first tool half 18 to the feed runner 22 in the second tool half 20, and into the flowing material characterization channel 30 formed between the first tool half 18 and the second tool half 20. The characteristics of the material are measured as it flows through the predefined channel cross-section 32 of the flowing material characterization channel 30 at a set flow rate from the first end 34 to the second end 36. The material flow velocity is typically controlled by the plasticating injection unit 12. After a set run time, the tool 16 is separated to allow removal of the solidified material following the characterization test (as described above). The first tool half 18 and the second tool half 20 are then closed again and the characterization testing is repeated with the material flowing through at a different set flow rate. This is repeated for multiple set flow rates. After sufficient data is collected, the cartridge 40 is adjusted (either manually or with the automatic actuator) to create a flow a path from the plasticating injection unit 12 to a different flowing material characterization channel 30 (or the cartridge 40 is replaced with one having a different set of flowing material characterization channels 30). The characterization testing is repeated for this new flowing material characterization channel 30 for the same multiple set flow rates. In this way a profile of the characteristics of the material over a range of flow rates and over a range of flowing material characterization channels 30 is developed.

Generally, in production settings, plasticating injection units 12 are run at a steady cycle of producing molded parts. Steady consistent cycles are important to ensure that the thermal history on the material is the same for each characterization test run. When the plasticating injection units 12 is first started up, it takes some time for the unit to heat up to a steady state. During this time, the various components of the unit are not at their ideal temperature. This typically causes the early production cycles to have some flaws and the molded parts for these cycles are typically discarded. The start-up period to establish a plastic and mold thermal stability can easily take many characterization test runs. If the plasticating injection unit 12 is interrupted for some length of time, this steady state is disrupted and the unit has to again run through several more production cycles before the steady state is reached again, which is also true for material characterization testing. If the mold 16 has to be opened and the flowing material characterization channel 30 replaced, then time and materials are wasted as the plasticating injection unit 12 is reset to steady state. Material characterization testing using a cartridge 40 as shown in FIGS. 3A and 3B allows flowing material characterization channels 30 to be tested without having to disassemble the tool 16 thus saving both time and materials.

Having a cartridge 40 with multiple flowing material characterization channels 30 significantly reduces the cost of material characterization tests. One cartridge 40 allows for testing of a material across multiple channel configurations. If more tests need to be done, a series of cartridges 40 can be made having a range of flowing material characterization channels 30, each having a different predefined channel cross-section 32.

It is possible to have computerized controls for the plasticating injection unit 12 that will open and close the mold 16 as needed, run the material at the various flow rates, and move the cartridge 40 as needed through each flowing material characterization channels 30. This will further reduce the time and cost of running material characterization testing.

In embodiments of the material characterization system, measurements of the material could be made through a sensor located within the plasticating injection unit 12 and an additional sensor 26 located within the tool 16 to provide a characterization of the material as it flows through the system. In some embodiments, the plasticating injection unit 12 could have a pressure sensor 24 and an additional sensor 26 located in the flowing material characterization channel 30 for tracing pressure through that feed runner 22 and the flowing material characterization channel 30. The additional sensor 26 working in conjunction with the pressure sensor 24 could be used to indicate the position of the material relative to the pressure traces provided by the pressure sensor 24 to separate the pressure signal into data prior to the material arriving at the additional sensor 26 and data after the material arrives at the additional sensor 26. The sensor 24 could also limit data collection to record pressure developed by the material passing through the flowing material characterization channel 20 after the material passes the sensor 24. The velocity of the material flowing through the flowing material characterization channel 30 can also determined by measuring the time for the material to pass from the pressure sensor 24 to the additional sensor 26. The volumetric flow rate of the material through the flowing material characterization channel 30 is determined from the geometry of the predefined channel cross-section 32 and the velocity of the material. The sample rate of each sensor can be varied depending on the particular application, but it is preferred that the sensors collect data at a frequency of 10,000 hertz, but quality data can be collected at a frequency of 5,0000 hertz or less dependent on the injection velocity through the flowing material characterization channel 30.

The material characterization profile system and method as described herein can be used to determine an optimal fill time for molding injection molded plastic parts by identifying the critical velocity for the material flowing through a mold cavity. The critical velocity is where the thermal balance between heat gains in the material versus heat lost to the colder flow boundaries is significantly balanced. Under critical velocity conditions the material temperature is relatively constant as it flows through the flow channel and the development of a plastic frozen layer along the flow channel boundaries stabilizes and becomes more uniform. Under these conditions, the material temperature across a part forming cavity will be relatively uniform from the gate to end of fill. Under these uniform temperatures, the plastic part being formed will have less thermal variations which is one of the major causes of the development of residual stresses and warpage of injection molded parts. This critical velocity could be identified using the system and method disclosed herein for a material under a wide range of flow geometries and can provide the molder a target injection molding fill rate before the part is ever molded. This would allow for faster mold start-ups and process optimization.

One method for determining the critical velocity using the system described herein, is to measure material flows through flowing material characterization channels 30 that are open to atmosphere at various rates for a steady flush at a constant flow rate while pressure within the flowing material characterization channels 30 are being monitored. After the material exits from the flowing material characterization channel 30 to atmosphere, pressures will rise, lower, or become constant depending on the thermal changes within the material. Increasing pressure would be indicative of a cooling material and a thickening frozen layer meaning that the flow velocity is too low. Decreasing pressure would be indicative of a material having a flow velocity that is too high for the particular application as excessive frictional heating may melt the frozen layer back into a liquid state. A constant steady pressure indicates a constant thermal condition within the flowing material characterization channel 30, which means that the critical velocity has been identified. Data collected in this manner could also be recorded and contrasted to other molding studies of the same material to determine whether flow conditions for molded plastic parts are at their optimum conditions with a minimum of problems related to the development of residual stresses and warpage.

Material characterization profiles created as described herein can be used by those of skill in the art for many other purposes such as accurately predicting the behavior of a material as it flows through a plastication injection unit into a final product. This represents a significant improvement over prior art devices having the limitations as described above.

In another embodiment, material characterization profiles developed as described above can also be incorporated into mathematical models that could be incorporated into mold filling simulation programs that can predict material behavior in user-defined molds. The mold filling simulation program could provide the material characteristics to a user in a variety of useful formats, whether graphical, tabular, or otherwise. The methods described herein could be used to capture the detailed flow conditions of the material flowing through flowing material characterization channels 30 having a variety of predefined channel cross-section 32 geometries of the material characterization system 10 as described herein. Measurements recorded include flow velocities of the material through the flowing material characterization channels 30 and the pressure developed by the material as it flows through the flowing material characterization channels 30.

A computer mold filling simulation program can be prepared to model the entire flow of the material from the plasticating injection unit 12 through any connecting flow channels that connect to the flowing material characterization channels 30. The results of simulations made by the mold filling simulation program can be compared to the material characterization measurements recorded in the flowing material characterization channels 30 as described herein and adjustments made to the mold filling simulation program can be made as appropriate. Iterative flow simulations can be performed for further fine tuning as needed so that the predicted material flow velocities though the channels of the simulation closely approximate the actual measured flow velocities through the flowing material characterization channels 30. At a user-defined tolerance that should be less than 5% variation between the measured and simulated flow velocities through the flowing material characterization channels 30, the predicted pressures through the flowing material characterization channels 30 are then contrasted to the actual measured pressures to determine the accuracy and error of the mold filling simulation program through a wide range of injection velocities and channel geometries.

The method described herein also comprises the use of the data measured under the actual injection molding conditions to improve upon current solution methods used in mold filling simulation programs that are based on the coupling of mathematical models of isothermally derived viscosity characteristics with thermal and phase change models. A mathematical model could be developed that includes at least some measure of the actual non-isothermal material characterization, including components of what is now required to be calculated from a variety of material characterization methods that might include viscosity, thermal conductivity, melt density, etc., into a single or reduced number of mathematical models. It should also be recognized that the methods disclosed herein can improve upon current methods of developing material data used to mathematically model heat transfer through the laminates of the molten material and between the molten material and the mold. This includes mathematical models of the development of a frozen layer that develops during injection molding.

In contrast to prior art material characterization methods that only characterize the rheology of a plastic material, material characterization system 10 and method as described herein directly estimates the pressure to fill a runner or cavity in an injection mold. In particular the material characterization system 10 and method provides an accurate means of evaluating the relative injection moldability of various plastic materials. The material characterization system 10 and method measures the pressure resulting in driving a molten polymer through the various predefined channel cross-section 32, whether runner-like or cavity-like, in the plurality of flowing material characterization channels 30 as described herein. Knowing the length of the flowing material characterization channels 30 and material flow velocity through these channels can provide data in the form of pressure per unit length of flow at a given injection velocity through a variety of predefined channel cross-section 32 which can be graphed as shown for example in FIG. 4. If the measured pressure of the melted material traveling through a four inches long by 0.040 inches thick channel in 1 second is 16,000 psi, then the pressure is expressed as 4,000 psi/inch at a 5 inch/second velocity.

Figure 4:
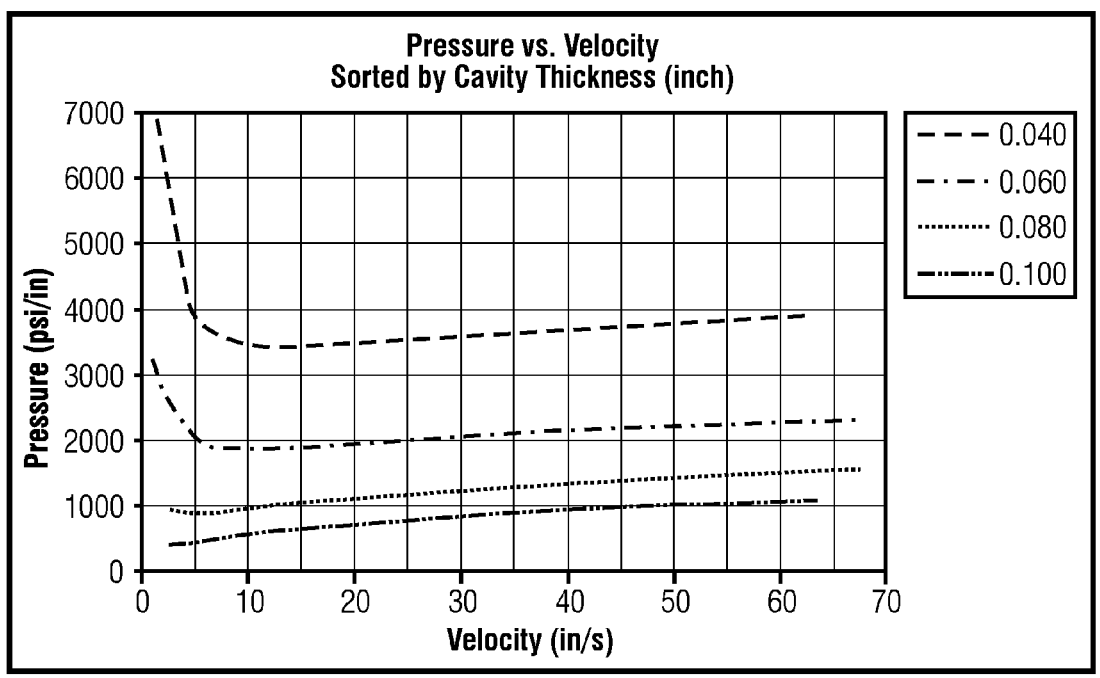
FIG. 4 is an example of a graph plotting data collected from a material characterization test as described herein.

Through this relatively low cost and efficient method, the level of information could be a portion of the materials characterization profile that would include multiple injection velocities through a number of flowing material characterization channels 30 having various predefined channel cross-sections 32 with runner-like and cavity-like geometries. The graph of FIG. 4 shows how the pressure/inch of flow is plotted against the injection speed (inch/second) through cavity-like geometries at thicknesses of 0.040 inches, 0.060 inches, 0.080 inches, and 0.100 inches. This method of mapping the material characteristics through different predefined channel cross-section 32 geometries and different injection velocities provides a fast, simple, low-cost way to estimate a mold's filling pressure and to contrast the potential injection moldability characteristics of various polymers.

An example of an application of this data would be in estimating the pressure to fill a product having a 1-mm wall thickness and having a flow length of 6 inches. From the injection moldability material characterization testing described herein, the designer could estimate from this data that it would take 24,000 psi to fill the part forming cavity. This exceeds the pressure limits of many plasticating injection units, and does not even consider the pressure required to fill the runners delivering the melted material to the mold cavity. As a result the designer could quickly react and evaluate whether another fill rate or wall thickness might be better suited to create this part.

Using flowing material characterization channels 30 that are open to atmosphere or to an oversized collection chamber allows for a wide range of tests to be completed quickly and economically. This minimizes the resistance to material flow that is created in the flowing material characterization channels 30 by the compression of air that results in a closed cavity and more closely represents the basic flow solutions that are commonly modeled by mold filling simulation programs. Most mold filling simulation programs ignore material flow resistance due to air compression because it is a more complex problem requiring the coupling of solutions for flow velocity with the simultaneous solution of air pressure buildup from an advancing flow front in a closed channel. Basing the mold filling simulation program on flow channels that are open to atmosphere provides a more direct means of measuring the accuracy of the basic simulation without the need to consider the added complexity introduced by air.

The material characterization profiles herein generated can also be used as a calibrating tool for existing prior-art mold filling simulation programs by comparing the characteristics of the material predicted by such programs against the measured material characterization profiles from the system described herein. Conducting mold filling simulation program validation by measuring material flow through flowing material characterization channels 30 that have simple predefined channel cross-section 32 geometries with a constant shape and no bends or turns, provides feedback on flow behavior in the most basic conditions. From this data an analyst can accurately determine the percentage of error existing in the programs under various conditions with the most fundamental channel geometries.

The actual measured data can be contrasted to simulation results in a number of different ways. For example, for a given predefined channel cross-section 32 of a flowing material characterization channel 30, a percentage of error at a given shear rate can be provided. If at a shear rate in a given cross-section geometry, the mold filling simulation program is found to be over predicting pressure by 30%, the analyst can use this information to adjust his assumptions when performing an injection molding simulation on an unrelated part having a similar wall thickness or runner cross section geometry. A developer of mold filling simulation programs would be able to use this wide range of contrasted data to quickly assess code performance and make adjustments to more closely approximate actual measured conditions. Additional complexity could be incorporated into the mold filling simulation programs by using flowing material characterization channels 30 that incorporate more complex predefined channel cross-sections 32 and/or include non-linear flow paths such as 90-degree bends, curves, spirals, diverging or converging flow effect, etc. In a similar manner, the material characterization profile provided by the mold filling simulation program could also be used to evaluate the performance of particular plasticating injection units 12.

The system and method disclosed herein can also directly be used to evaluate the performance of particular plasticating injection units 12. In this application, by using flowing material characterization channels 30 that incorporate a variety of predefined channel cross-sections 32 from the simple ones described herein to more complex cross-sections, gating conditions, and/or flow paths that include non-linear flow paths such as 90-degree bends, curves, spirals, diverging or converging flow effect, etc. It should be understood that the flowing material characterization channels 30 could have many variations from the first end 34 to the second end 36, including flow paths that diverge and/or converge and with transitions that may be abrupt or gradual. In addition, while the material characterization channels 30 have been shown with uniform predefined channel cross-sections 32, it will be understood that the width or thickness can also be varied from the first end 34 to the second end 36. The sensors in the material characterization system 10 allow accurate, quick, and economical measurements of flow rates and pressures through and within the flowing material characterization channels 30 which can be contrasted to the plasticating injection unit's 12 input to determine actual performance.

The material characterization system 10 and the method of using the system as described herein can be used to correct for material temperature variations that can develop as material flows through any material delivery flow channels that connect the material source to the flowing material characterization channels 30. This can be done by using a mold filling simulation program. The mold filling simulation program is run to predict flow and material conditions from the plastification injection unit 12, through the sprue 21, runner section 22, and the flowing material characterization channels 30. The material temperature rise or drop through each of the sprue 21, runner section 22, and the flowing material characterization channels 30, and the pressure and flow velocity through the flowing material characterization channels 30 are calculated. The mold filling simulation program is run a second time on only the flowing material characterization channels 30 using as a material input a material having a temperature as predicted by the flow simulation program to be entering the flowing material characterization channels 30.

Figure 5A:
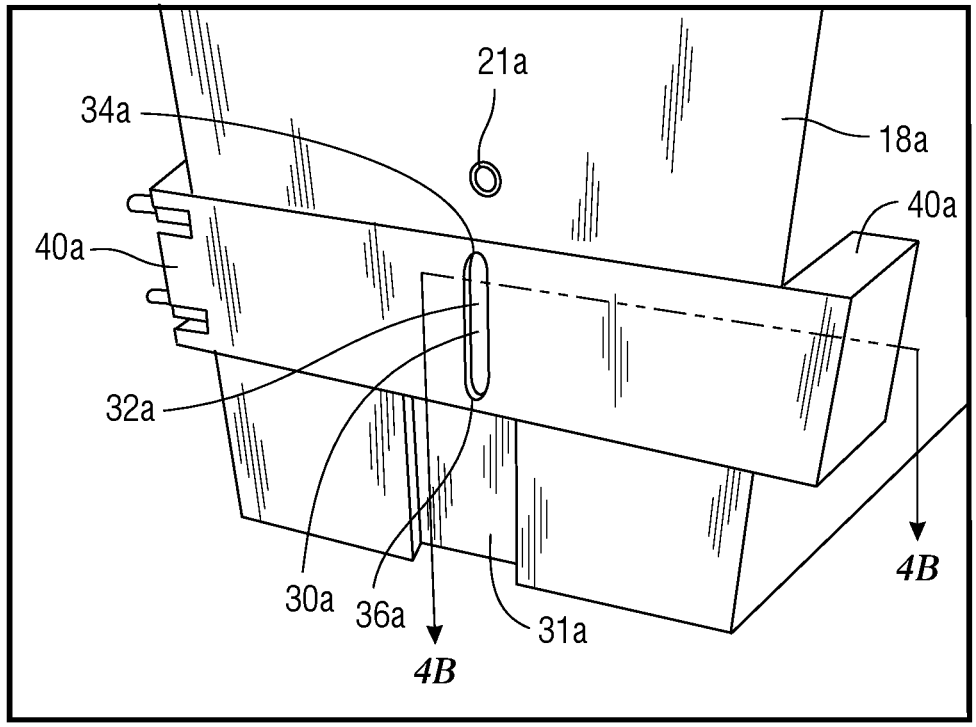
FIG. 5A is a perspective view of another embodiment of the first tool half.

FIG. 5A shows another embodiment of the material characterization system 10a in which the first tool half 18a has an adjustable and removable cartridge 40a that comprises a single flowing material characterization channels 30a impressed into it. When both the first tool half 18a and second tool half 20a are inserted into the material characterization system 10a, the flowing material characterization channel 30a is encapsulated along a central plane within the tool 16a. One having ordinary skill in the art will see that the flowing material characterization channel 30a can be directly impressed into the first tool half 18a without the cartridge 40a and that the tool 16a in its entirety is the adjustable element. Although impractical to do, it will be understood that the tool 16a could be oriented in such a manner that the second tool half 20a comprises the cartridge 40a with the plurality of flowing material characterization channels 30a and the first tool half 18a comprises the sensors, while still achieving similar results from the system. As discussed above, having a single flowing material characterization channel 30a is not preferred because of the costs associated with having to create separate mold components for each flowing material characterization channel 30a.

Figure 5B:
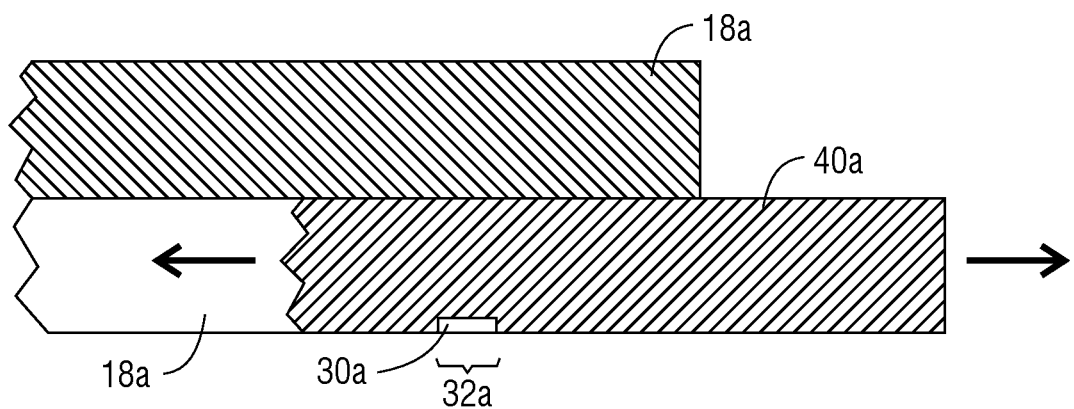
FIG. 5B is a cross section of the cartridge of the first tool half of FIG. 4A.

In this embodiment, the flowing material characterization channels 30a comprises a first end 34a and a second end 36a, having a predefined channel cross-section 32a geometry. When the tool 16a is installed within the material characterization system 10a, the side of each predefined channel cross-section 32a against the second tool half 20a is entirely flat; whereas, the side of the predefined channel cross-section 32a impressed into the first tool half 18a forms into the shape of the predefined channel cross-section 32a geometry. The geometry of the predefined channel cross-section 32a of the flowing material characterization channel 30a, as shown in FIG. 5B, is rectangular and uniform from the first end 34a to the second end 36a of the flowing material characterization channel 30a. It will be understood that other geometries of the predefined channel cross-section 32a may be used within the material characterization system 10a.

The cartridge 40a can be adjusted by an actuator device (not shown) that allows for the user to adjust the cartridge 40a without having to remove the entire tool 16a from the system. The actuator may make adjustments of the cartridge 40a manually or automatically. The cartridge 40a can be swapped out entirely with another one that has a different one or set of flowing material characterization channels 30a, each with different predefined channel cross-section 32a geometries. This allows for quicker characterization of a material with the method described above.

The second end 36a of the flowing material characterization channel 30a can be varied. The flowing material characterization channel 30a shown in FIG. 5A has a second end 36a that is closed off, allowing for the flowing material characterization channel 30a to be completely sealed and pressurized. Other flowing material characterization channels 30a may have a second end 36a that opens to the surrounding atmosphere which allows for characterization for materials under those conditions as previously described. Having the ability to quantify the characteristics of the material in a pressurized flowing material characterization channel 30a and in a non-pressurized flowing material characterization channel 30a can give a broader and more accurate understanding of the flow characteristics of the material.

Figure 6:
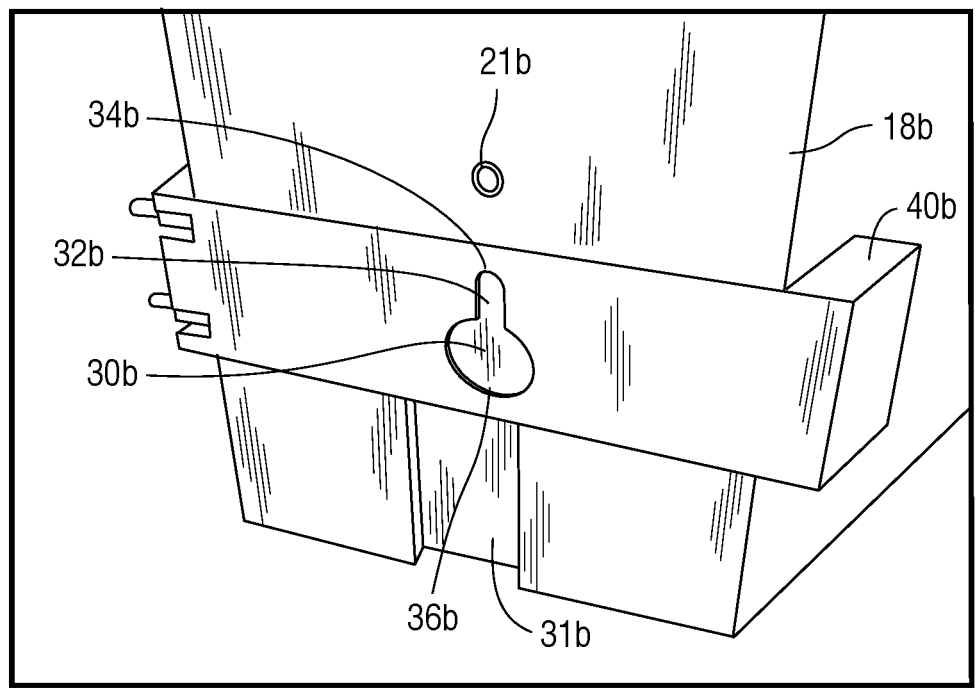
FIG. 6 is a perspective view of another embodiment of the first tool half.

FIG. 6 shows another embodiment in which the cartridge 40b has a flowing material characterization channel 30b having a non-linear flow path from the first end 34b to second end 36b. The second end 36b is a collection region 42b for the material to form into after running the length of the entire flowing material characterization channel 30b. The geometry of the predefined channel cross-section 32b of the flowing material characterization channel 30b opens up in the downstream portion of the channel so that the collection region 42b has its own independent cross-section geometry. The actual dimensions of the collection region 42b can be varied to allow characterization of the material as it fills a variety of shapes of collection regions 42b. It is understood, that such non-linear flow paths can be incorporated into cartridges 40b having a plurality of flowing material characterization channel 30b.

Figure 7:
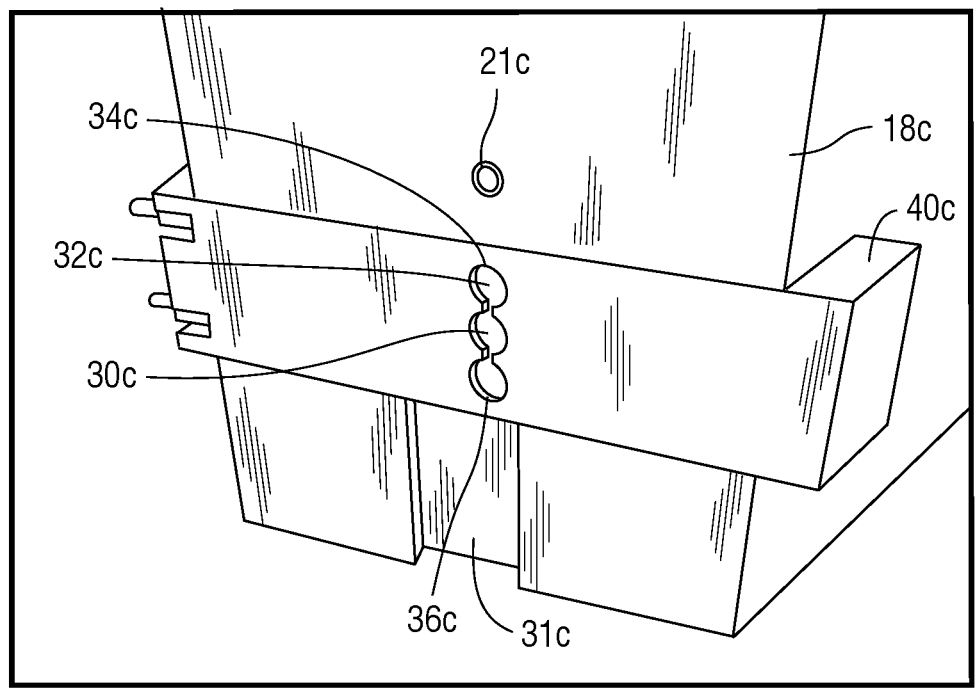
FIG. 7 is a perspective view of another embodiment of the first tool half.

FIG. 7 shows another embodiment in which the cartridge 40c has a flowing material characterization channel 30c in which the flow path from the first end 34c to second end 36c is much more complicated than a linear channel or a simple flowing material collection region of earlier embodiments. This is provided to illustrate that the system and method described herein could be used to provide material characterization in a variety of flowing material characterization channel 30c shapes and configurations. It is understood, that such non-linear flow paths can be incorporated into cartridges 40c having a plurality of flowing material characterization channel 30c.

In other embodiments not shown, the cartridge could have other configurations. For example, the cartridge could be a circular movable element that is rotatable around the sprue. In this embodiment, the plurality of flowing material characterization channels are incorporated around the circumference of the sprue with their first ends closer to the sprue and their second ends towards the other circumference of the cartridge. Selecting a different flowing characterization channel is simply a matter of rotating the cartridge to line up with the feed runner and create a flow path from the plasticating injection unit to the selected flowing characterization channel. This embodiment is limited in that not as many flowing characterization channels can be incorporated in a circular cartridge as compared to the rectangular cartridge shown in FIG. 3A. Furthermore, swapping out a circular cartridge for another having a different configuration of flowing characterization channels would be more complicated than sliding out a rectangular cartridge from the tool.

This invention has been described with reference to several preferred embodiments. Many modifications and alterations will occur to others upon reading and understanding the preceding specification. It is intended that the invention be construed as including all such alterations and modifications in so far as they come within the scope of the appended claims or the equivalents of these claims.

The invention claimed is:

1. A material characterization system for quantifying the characteristics of a thermoplastic material melted into a fluid state by a plasticating injection unit, the system comprising:
   a tool comprising a first tool half, a second tool half, a plurality of flowing material characterization channels on an adjustable and removable cartridge, and a feed runner having a flow path to said plasticating injection unit;
   said tool is at a temperature that causes phase changes from fluid to solid to occur in at least a portion of the material being characterized and that enables a solidification of the material in said flowing material characterization channel;
   each of said plurality of flowing material characterization channels having a first end, a second end, and a predefined channel cross-section geometry;
   said feed runner connectable to a single said flowing material characterization channel in succession at said first end, extending the flow path from the plasticating injection unit to said flowing material characterization channel;
   said tool is adjustable to disconnect said feed runner from said flowing material characterization channel and connect said feed runner to a different flowing material characterization channel; and
   a sensor for quantifying the characteristics of the material under different flow conditions.

2. The material characterization system of claim 1 wherein said tool is adjusted by adjusting said cartridge.

3. The material characterization system of claim 1 wherein said tool is adjusted by adjusting said cartridge; and
   said cartridge is automatically adjustable by an actuator.

4. The material characterization system of claim 1 wherein said second end of one of said plurality of flowing material characterization channels is closed and can be pressurized.

5. The material characterization system of claim 1 wherein the second end of one of said plurality of flowing material characterization channels is open to atmosphere.

6. The material characterization system of claim 1 wherein said second end of one of said plurality of flowing material characterization channels is a collection region.

7. The material characterization system of claim 1 wherein said predefined channel cross-section of one of said plurality of flowing material characterization channels is not uniform in geometry between said first end and said second end.

8. The material characterization system of claim 1 wherein the geometry of said predefined channel cross-section of one of said plurality of flowing material characterization channels is circular, rectangular, trapezoidal, or parabolic.

9. The material characterization system of claim 1 wherein one of said plurality of flowing material characterization channels defines a linear flow path.

10. The material characterization system of claim 1 wherein one of said plurality of flowing material characterization channels defines a non-linear flow path.

11. The material characterization system of claim 1 further comprising an additional sensor for quantifying the characteristics of the material.

12. The material characterization system of claim 1 further comprising the plasticating injection unit has a pressure sensor for tracing pressure through said feed runner and said flowing material characterization channels.

13. The material characterization system of claim 1 further comprising:
   the plasticating injection unit has a pressure sensor for tracing pressure through said feed runner and said flowing material characterization channel; and
   said sensor working in conjunction with said pressure sensor for indicating the position of the material relative to the pressure traces provided by said pressure sensor to separate the pressure signal into data prior to the material arriving at said sensor and after arriving at said sensor.

14. The material characterization system of claim 1 wherein said sensor for recording the pressure developed by the material passing through said flowing material characterization channel after the material passes said sensor.

15. The material characterization system of claim 1 wherein the plasticating injection unit controls the velocity of the material.

16. The material characterization system of claim 1 wherein the velocity of the material is determined by the volumetric flow rate provided by the plasticating injection unit and said predefined channel cross-section.

17. The material characterization system of claim 1 wherein said sensor is a pressure sensor.

18. The material characterization system of claim 1 wherein said sensor is a thermocouple.

19. The material characterization system of claim 1 wherein said sensor is a position sensor.

20. The material characterization system of claim 1 wherein said sensor is a combination of sensor types.

21. The material characterization system of claim 1 further comprising:
   an additional sensor for quantifying the characteristics of the material;
   said sensor and additional sensor located in said flowing material characterization channel; and
   the velocity of the material flowing through said flowing material characterization channel is determined by measuring the time for the material to pass from said sensor to said additional sensor.

22. The material characterization system of claim 1 further comprising:
   an additional sensor for quantifying the characteristics of the material;
   said sensor and additional sensor located in said flowing material characterization channel;
   the velocity of the material flowing through said flowing material characterization channel is determined by measuring the time for the material to pass from said sensor to said additional sensor; and
   the volumetric flow rate of the material through said flowing material characterization channel is determined from said predefined channel cross-section and the velocity of the material.

23. The material characterization system of claim 1 wherein said sensor collects data at a frequency of at least 5,000 hertz.

24. The material characterization system of claim 1 wherein said sensor collects data at a frequency of at least 10,000 hertz.

25. A method of quantifying the characteristics of a flowing thermoplastic material to determine its behavior in a plasticating injection unit comprising:
(1) connecting a tool comprising a plurality of flowing material characterization channels on an adjustable and removable cartridge, each having a predetermined cross-sectional geometry, to the plasticating injection unit;
(2) melting the material into a fluid state with the plasticating injection unit;
(3) flowing the material through a single flowing material characterization channel at multiple set flow rates;
(4) measuring the material characteristics through the single flowing material characterization channel at the multiple set flow rates;
(5) repeating steps (1) through (4) for a different flowing material characterization channel from the plurality of flowing material characterization channels, by adjusting and/or removing said cartridge.

26. The method of quantifying the characteristics of a flowing thermoplastic material of claim 25, further comprising incorporating the measured characteristics of the material from each flowing material characterization channel into a mold filling simulation program.

27. The method of quantifying the characteristics of a flowing thermoplastic material of claim 25 further comprising:
calculating the differences between the characteristics of the material through each flowing material characterization channel against predicted material behavior generated through a mold filling simulation program; and
using these calculated differences to validate the predicted material behavior of the mold filling simulation program.

28. The method of quantifying the characteristics of a flowing thermoplastic material of claim 25 further comprising:
calculating the velocity of the material flowing through each flowing material characterization channel by measuring the time for the material to pass between two sensors within a single flowing material characterization channel at multiple set flow rates; and
calculating the volumetric flow rate of the material through the flowing material characterization channel from the predefined channel cross-section and the velocity of the material.

29. The method of quantifying the characteristics of a flowing thermoplastic material of claim 25 further comprising providing the characteristics of the material in graphical format.

30. The method of quantifying the characteristics of a flowing thermoplastic material of claim 25 further comprising providing the characteristics of the material in tabular format.

31. The method of quantifying the characteristics of a flowing thermoplastic material of claim 25 further comprising evaluating the performance of the plasticating injection unit through the quantified characteristics of the material from each flowing material characterization channel.

32. The method of quantifying the characteristics of a flowing thermoplastic material of claim 25 wherein the pressure per inch of flow of the material flowing through each flowing material characterization channel is calculated.

33. The method of quantifying the characteristics of a flowing thermoplastic material of claim 25 wherein the characteristics of a developing frozen layer of material skin within each flowing material characterization channel is calculated.

34. The method of quantifying the characteristics of a flowing thermoplastic material of claim 25 wherein the characteristics of the material are measured through a sensor.

35. The method of quantifying the characteristics of a flowing thermoplastic material of claim 25 wherein the characteristics of the material are measured through a pressure sensor and a thermocouple.

36. The method of quantifying the characteristics of a flowing thermoplastic material of claim 25 wherein the characteristics of the material are measured through a plurality of sensors.

37. The method of quantifying the characteristics of a flowing thermoplastic material of claim 25 wherein the characteristics of the material are measured through a plurality of thermocouples.

38. The method of quantifying the characteristics of a flowing thermoplastic material of claim 25 wherein the characteristics of the material are measured at a frequency of at least 5,000 hertz.

39. The method of quantifying the characteristics of a flowing thermoplastic material of claim 25 wherein the characteristics of the material are measured at a frequency of at least 10,000 hertz.

40. A material characterization system for quantifying the characteristics of a developing frozen layer occurring in a laminar flowing thermoplastic material, the developing frozen layer developing in the outer laminates between the laminar flowing material and a relatively lower temperature flowing material characterization channel, the laminar flowing thermoplastic material melted into a fluid state by a plasticating injection unit, the system comprising:
a tool comprising a first tool half, a second tool half, a plurality of flowing material characterization channels on an adjustable and removable cartridge, and a feed runner having a flow path to said plasticating injection unit;
said tool is at a temperature that causes phase changes from fluid to solid to occur in at least the outer laminates of the material being characterized and that enables solidification of the material in said flowing material characterization channel;
each of said plurality of flowing material characterization channels having a first end, a second end, and a predefined channel cross-section geometry;
said feed runner connectable to a single said flowing material characterization channel in succession at said first end, extending the material flow path from said plasticating injection unit to said material flow characterization channel;
said tool is adjustable to disconnect said feed runner from said flowing material characterization channel and connect said feed runner to a different flowing characterization channel; and
a sensor for quantifying the characteristics of the developing frozen layer of the material under different flow conditions.

41. The material characterization system of claim 40 wherein: said tool is adjusted by adjusting said cartridge.

42. The material characterization system of claim 40 wherein: said tool is adjusted by adjusting said cartridge; and said cartridge is automatically adjustable by an actuator.

43. The material characterization system of claim 40 wherein said second end of one of said plurality of flowing material characterization channels is closed and can be pressurized.

44. The material characterization system of claim 40 wherein the second end of one of said plurality of flowing material characterization channels is open to atmosphere.

45. The material characterization system of claim 40 wherein said second end of one of said plurality of flowing material characterization channels is a collection region.

46. The material characterization system of claim 40 wherein said predefined channel cross-section of one of said plurality of said flowing material characterization channels is not uniform in geometry between said first end and said second end.

47. The material characterization system of claim 40 wherein the geometry of said predefined channel cross-section of one of said plurality of said flowing material characterization channels is circular, rectangular, trapezoidal, or parabolic.

48. The material characterization system of claim 40 wherein one of said plurality of flowing material characterization channels defines a linear flow path.

49. The material characterization system of claim 40 wherein one of said plurality of flowing material characterization channels defines a non-linear flow path.

50. The material characterization system of claim 40 further comprising an additional sensor for quantifying the characteristics of the material.

51. The material characterization system of claim 40 further comprising the plasticating injection unit has a pressure sensor for tracing pressure through said feed runner and said flowing material characterization channel.

52. The material characterization system of claim 40 further comprising:
the plasticating injection unit has a pressure sensor for tracing pressure through said feed runner and said flowing material characterization channel; and
said sensor working in conjunction with said pressure sensor for indicating the position of the material relative to the pressure traces provided by said pressure sensor to separate the pressure signal into data prior to the material arriving at said sensor and after arriving at said sensor.

53. The material characterization system of claim 40 wherein said sensor is for recording the pressure developed by the material passing through said flowing material characterization channel after the material passes said sensor.

54. The material characterization system of claim 40 wherein the plasticating injection unit controls the velocity of the material.

55. The material characterization system of claim 40 wherein the velocity of the material is determined by the volumetric flow rate provided by the plasticating injection unit and said predefined channel cross-section.

56. The material characterization system of claim 40 wherein said sensor is a pressure sensor.

57. The material characterization system of claim 40 wherein said sensor is a thermocouple.

58. The material characterization system of claim 40 wherein said sensor is a position sensor.

59. The material characterization system of claim 40 wherein said sensor is a combination of sensor types.

60. The material characterization system of claim 40 further comprising:
an additional sensor for quantifying the characteristics of the material;
said sensor and additional sensor located in said flowing material characterization channel; and
the velocity of the material flowing through said flowing material characterization channel is determined by measuring the time for the material to pass from said sensor to said additional sensor.

61. The material characterization system of claim 40 further comprising:
an additional sensor for quantifying the characteristics of the material;
said sensor and additional sensor located in said flowing material characterization channel;
the velocity of the material flowing through said flowing material characterization channel is determined by measuring the time for the material to pass from said sensor to said additional sensor; and
the volumetric flow rate of the material through said flowing material characterization channel is determined from said predefined channel cross-section and the velocity of the material.

62. The material characterization system of claim 40 wherein said sensor collects data at a frequency of at least 5,000 hertz.

63. The material characterization system of claim 40 wherein said sensor collects data at a frequency of at least 10,000 hertz.

64. A method of quantifying the characteristics of a developing frozen layer occurring in a laminar flowing thermoplastic material, the developing frozen layer developing in the outer laminates between the laminar flowing material and a relatively lower temperature flowing material characterization channel, to determine the thermoplastic material's behavior in a plasticating injection unit comprising:
(1) connecting a tool comprising a plurality of flowing material characterization channels on an adjustable and removable cartridge, each having a predetermined cross-sectional geometry, to the plasticating injection unit;
(2) melting the material into a fluid state with the plasticating injection unit;
(3) flowing the material through a single flowing material characterization channel at multiple set flow rates;
(4) measuring the material characteristics of a developing frozen layer occurring in the material through the single flowing material characterization channel at the multiple set flow rates; and
(5) repeating steps (1) through (4) for a different flowing material characterization channel from the plurality of flowing material characterization channels, by adjusting and/or removing said cartridge.

65. The method of quantifying the characteristics of a developing frozen layer occurring in a laminar flowing thermoplastic material of claim 64 further comprising incorporating the measured characteristics of the developing frozen layer occurring in the material from each flowing material characterization channel into a mold filling simulation program.

66. The method of quantifying the characteristics of a developing frozen layer occurring in a laminar flowing thermoplastic material of claim 64 further comprising:
calculating the differences between the characteristics of the developing frozen layer occurring in the material through each flowing material characterization channel against predicted material behavior generated through a mold filling simulation program; and using these calculated differences to validate the predicted material behavior of the mold filling simulation program.

67. The method of quantifying the characteristics of a developing frozen layer occurring in a laminar flowing thermoplastic material of claim 64 further comprising:
calculating the differences between the characteristics of the developing frozen layer occurring in the material through each flowing material characterization channel against a material characterization system not accounting for the developing frozen layer occurring in the material; and
using these calculated differences to contrast the characteristics of the developing frozen layer occurring in the material through each flowing material characterization channel against the material characterization system not accounting for the developing frozen layer occurring in the material.

68. The method of quantifying the characteristics of a developing frozen layer occurring in a laminar flowing thermoplastic material of claim 64 further comprising:
calculating the velocity of the developing frozen layer occurring in the material flowing through each flowing material characterization channel by measuring the time for the material to pass between two sensors within a single flowing material characterization channel at multiple set flow rates; and
calculating the volumetric flow rate of the material flowing through the flowing material characterization channel from the predefined channel cross-section and the velocity of the material.

69. The method of quantifying the characteristics of a developing frozen layer occurring in a laminar flowing thermoplastic material of claim 64 further comprising providing the characteristics of the developing frozen layer occurring in the material in graphical format.

70. The method of quantifying the characteristics of a developing frozen layer occurring in a laminar flowing thermoplastic material of claim 64 further comprising providing the characteristics of the developing frozen layer occurring in the material in tabular format.

71. The method of quantifying the characteristics of a developing frozen layer occurring in a laminar flowing thermoplastic material of claim 64 further comprising evaluating the performance of the plasticating injection unit through the quantified characteristics of the developing frozen layer occurring in the material from each flowing material characterization channels.

72. The method of quantifying the characteristics of a developing frozen layer occurring in a laminar flowing thermoplastic material of claim 64 wherein the pressure per inch of flow of the material flowing through each flowing material characterization channels is calculated.

73. The method of quantifying the characteristics of a developing frozen layer occurring in a laminar flowing thermoplastic material of claim 64 wherein the characteristics of a developing frozen layer occurring in the material are measured through a sensor.

74. The method of quantifying the characteristics of a developing frozen layer occurring in a laminar flowing thermoplastic material of claim 64 wherein the characteristics of a developing frozen layer occurring in the material are measured through a pressure sensor and a thermocouple.

75. The method of quantifying the characteristics of a developing frozen layer occurring in a laminar flowing thermoplastic material of claim 64 wherein the characteristics of a developing frozen layer occurring in the material are measured through a plurality of sensors.

76. The method of quantifying the characteristics of a developing frozen layer occurring in a laminar flowing thermoplastic material of claim 64 wherein the characteristics of a developing frozen layer occurring in the material are measured through a plurality of thermocouples.

77. The method of quantifying the characteristics of a developing frozen layer occurring in a laminar flowing thermoplastic material of claim 64 wherein the characteristics of the developing frozen layer occurring in the material are measured at a frequency of at least 5,000 hertz.

78. The method of quantifying the characteristics of a developing frozen layer occurring in a laminar flowing thermoplastic material of claim 64 wherein the characteristics of the developing frozen layer occurring in the material are measured at a frequency of at least 10,000 hertz.

79. The method of quantifying the characteristics of a developing frozen layer occurring in a laminar flowing thermoplastic material of claim 64 wherein step (4) further comprises measuring the characteristics of the laminar flowing material inside the developing frozen layer occurring in the material through that material flow characterization channel at the multiple set flow rates.

80. The method of quantifying the characteristics of a developing frozen layer occurring in a laminar flowing thermoplastic material of claim 64 wherein step (4) further comprises:
measuring the characteristics of the laminar flowing material inside the developing frozen layer and the pressure per unit length of flow of the developing frozen layer occurring in the material, both measured through the flowing material characterization channel at the multiple set flow rates.

81. The method of quantifying the characteristics of a developing frozen layer occurring in a laminar flowing thermoplastic material of claim 64 wherein step (4) further comprises:
measuring the characteristics of the laminar flowing material inside the developing frozen layer occurring in the material through that material flow characterization channel at the multiple set flow rates; and
measuring the characteristics of the laminar flowing material inside the developing frozen layer, the shear rate of the developing frozen layer occurring in the material, and the shear stress of the developing frozen layer occurring in the material, each measured through the flowing material characterization channel at the multiple set flow rates.

82. The method of quantifying the characteristics of a developing frozen layer occurring in a laminar flowing thermoplastic material of claim 64 wherein step (4) further comprises:
measuring the characteristics of the laminar flowing material inside the developing frozen layer and the viscosity of the developing frozen layer occurring in the material, both measured through the flowing material characterization channel at the multiple set flow rates.

* * * * *